United States Patent
Park

(10) Patent No.: US 12,402,710 B2
(45) Date of Patent: Sep. 2, 2025

(54) COSMETIC INJECTOR ON WHICH MICRONEEDLES FOR INDUCING ABSORPTION OF COSMETICS ARE MOUNTED, AND MANUFACTURING METHOD THEREFOR

(71) Applicant: ILLON CO., LTD., Gyeonggi-do (KR)

(72) Inventor: Ramee Park, Gyeonggi-do (KR)

(73) Assignee: ILLON CO., LTD., Gyeonggi-do (KR)

( * ) Notice: Subject to any disclaimer, the term of this patent is extended or adjusted under 35 U.S.C. 154(b) by 721 days.

(21) Appl. No.: 17/787,169

(22) PCT Filed: Mar. 4, 2021

(86) PCT No.: PCT/KR2021/002641
§ 371 (c)(1),
(2) Date: Jun. 17, 2022

(87) PCT Pub. No.: WO2021/206294
PCT Pub. Date: Oct. 14, 2021

(65) Prior Publication Data
US 2023/0014809 A1    Jan. 19, 2023

(30) Foreign Application Priority Data

Apr. 6, 2020    (KR) .......................... 10-2020-0041515
Apr. 6, 2020    (KR) .......................... 10-2020-0041529

(51) Int. Cl.
*A45D 34/04*    (2006.01)
*A61M 37/00*    (2006.01)

(52) U.S. Cl.
CPC ......... *A45D 34/04* (2013.01); *A61M 37/0015* (2013.01); *A61M 2037/0023* (2013.01); *A61M 2037/0061* (2013.01)

(58) Field of Classification Search
CPC .............. A45D 34/04; A61M 37/0015; A61M 2037/0023; A61M 2037/0061; A61M 2037/003; A61M 2037/0046
See application file for complete search history.

(56) References Cited

U.S. PATENT DOCUMENTS

2004/0265365 A1    12/2004    Daddona et al.

FOREIGN PATENT DOCUMENTS

| EP | 3111987 A1 | 1/2017 |
| KR | 101710887 A | 2/2017 |
| KR | 101710887 B1 * | 3/2017 |

OTHER PUBLICATIONS

The extended European search report of EP21 78 4757, Apr. 8, 2024.

* cited by examiner

Primary Examiner — Theodore J Stigell
(74) Attorney, Agent, or Firm — STIP Law Group, LLC

(57) ABSTRACT

A cosmetic injector includes an accommodation part for accommodating cosmetics; a head part having a flow path through which cosmetics flow; a microneedle part fixed to the head part, and inserted into the skin so as to cause the cosmetics to penetrate the skin; and a pumping part for transferring, to the head part, the cosmetics accommodated in the accommodation part. The head part includes: a first head part for receiving the cosmetics from the pumping part; and a second head part coupled to the upper portion of the first head part, and the microneedle part includes: a microneedle plate provided between the first head part and the second head part; and a plurality of microneedles which extend from the microneedle plate so as to protrude toward the upper surface of the second head part, and which guide, into the skin, the cosmetics discharged from the head part.

11 Claims, 11 Drawing Sheets

(a)

(b)

US 12,402,710 B2

COSMETIC INJECTOR ON WHICH MICRONEEDLES FOR INDUCING ABSORPTION OF COSMETICS ARE MOUNTED, AND MANUFACTURING METHOD THEREFOR

This application is a 371 of International Application No. based on PCT/KR2021/002641 filed on Mar. 4, 2021 which claims priority to Korean Application No. 10-2020-0041515, filed Apr. 6, 2020 and Korean Application No. 10-2020-0041529, filed Apr. 6, 2020, both of which are incorporated by reference, as if fully set forth herein.

TECHNICAL FIELD

The present invention relates to a cosmetic injector, on which microneedles for inducing absorption of cosmetics are mounted, and a manufacturing method therefor.

BACKGROUND ART

Human skin is made of an epidermal layer and a dermal layer including collagen, and the amount of collagen in the dermal layer decreases as aging progresses. Accordingly, the skin becomes dry or wrinkled, which reduces the elasticity of the skin.

Therefore, nutrients such as vitamins or peptides that help collagen production are applied to the skin so as to keep the skin elastic. In general, the amount of nutrients, which are applied to the skin, pass through the epidermal layer, and are then absorbed into the dermal layer, is only 0.3% of the total content.

In order to solve the above limitation, a method of directly injecting nutrients into the subcutaneous tissue using a syringe is employed. This method also has several limitations, such as causing bleeding, pain, and inflammatory reactions, and leaving scars. Also, it may be difficult to apply this method depending on ages or skin characteristics.

As an alternative to this method, a method of injecting nutrients into the subcutaneous tissue by making micro-gaps in the skin using a microneedle is emerging.

This method can minimize pain, bleeding, and inflammatory reactions when injecting nutrients, and enables local injection of the nutrients, thus making it possible to effectively and continuously inject the nutrients only into desired areas. Therefore, this method is being actively studied.

The microneedle is usually a metal which has a tip made of micro units, and a cosmetic injector using a microneedle according to the related art has a structure in which a plurality of microneedles are individually mounted to a head part.

Therefore, there is a limitation in that each microneedle has to be mounted on the head part when manufacturing an instrument, and each microneedle can be broken and stuck in the skin while being inserted into the subcutaneous tissue and cause inflammatory reactions or other diseases.

DISCLOSURE OF THE INVENTION

Technical Problem

The purpose of the present invention is to provide a cosmetic injector in which a microneedle can be easily mounted on a head part.

Also, the purpose of the present invention is to prevent a microneedle mounted on a head part from being broken.

Also, the purpose of the present invention is to prevent a microneedle from being contaminated by an operator when a cosmetic injector is manufactured.

Technical Solution

According to an embodiment of the present invention, provided is a cosmetic injector, on which microneedles for inducing absorption of cosmetics are mounted, the cosmetic injector including: an accommodation part configured to accommodate cosmetics; a head part having a flow path through which the cosmetics flow in; a microneedle part which is fixed to the head part, and which is inserted into the skin and allows the cosmetics to penetrate the skin; and a pumping part configured to transfer, to the head part, the cosmetics accommodated in the accommodation part, wherein the head part comprises: a first head part configured to receive the cosmetics from the pumping part; and a second head part coupled to the upper portion of the first head part, wherein the microneedle part comprises: a microneedle plate provided between the first head part and the second head part; and a plurality of microneedles which extend from the microneedle plate and protrude toward the upper surface of the second head part, and which guide, into the skin, the cosmetics discharged from the head part.

In an embodiment, the microneedle plate and the plurality of microneedles may be integrally formed.

In an embodiment, the first head part may include: a first head part body having the upper surface on which the microneedle plate rests; and a resting protrusion having the outer circumferential surface that contacts the plurality of microneedles.

In an embodiment, the resting protrusion may be provided in plurality.

In an embodiment, the microneedle plate has a resting protrusion through-hole through which the resting protrusion passes.

In an embodiment, the plurality of microneedles may extend upward from the vicinity of the resting protrusion through-holes of the microneedle plate or from edges of the microneedle plate.

In an embodiment, the microneedle part may be made of metal so that contact points between the microneedle plate and the plurality of microneedles are pressed and bent by the resting protrusion.

In an embodiment, the second head part may include a second head part body having the lower surface that contacts the microneedle plate, and the second head part body may have a resting protrusion coupling part that is a hole into which the resting protrusion and the plurality of microneedles are inserted.

In an embodiment, gaps configured to accommodate the plurality of microneedles may be formed between the resting protrusion coupling part and the resting protrusion or between the outer boundary of the second head part body and the resting protrusion.

In an embodiment, the length of each of the plurality of microneedles may be greater than the distance from the upper surface of the first head part body to the upper surface of the second head part.

In an embodiment, the cosmetic injector may further include a head housing that accommodates the first head part, the second head part, and the microneedle part, and receives the cosmetics from the pumping part.

In an embodiment, the first head part body may have: a guide hole that vertically passes through the first head part body; and a first head part flow path which is provided in the lower portion of the first head part body and formed radially about the guide hole, wherein the cosmetics, which have flowed into the head housing via the pumping part, are guided to the guide hole via the first head part flow path.

In an embodiment, the second head part may include a second head part body having the lower surface that contacts the microneedle plate,
wherein the head housing further comprises:
a head housing body configured to accommodate the first head part, the second head part, and the microneedle part; and a fixing protrusion that protrudes from the head housing body, wherein the first head part further comprises a first head part fixing protrusion insertion hole through which the fixing protrusion passes, the microneedle part further comprises a microneedle part fixing protrusion insertion hole through which the fixing protrusion, which has passed through the first head part fixing protrusion insertion hole, passes, and the second head part further comprises a second head part fixing protrusion insertion hole through which the fixing protrusion, which has passed through the microneedle part fixing protrusion insertion hole, passes.

In an embodiment, the fixing protrusion may be provided in plurality, and the number of each of first head part fixing protrusion insertion holes, microneedle part fixing protrusion insertion holes, and second head part fixing protrusion insertion holes may correspond to the number of fixing protrusions.

In an embodiment, when the head part is pressed toward the pumping part, the cosmetics, which have been supplied via the pumping part, may be discharged via the outer circumferential surfaces of the plurality of microneedles.

According to an embodiment of the present invention, provided is a method for manufacturing the cosmetic injector of claim 1, on which microneedles for inducing absorption of cosmetics are mounted, the method comprising: a resting operation of resting the microneedle plate on the upper surface of the first head part; and a head part coupling operation of coupling the second head part to the upper portion of the first head part.

In an embodiment, the microneedle part may be formed such that the microneedle plate and the plurality of microneedles are provided parallel to each other prior to performing the resting operation.

In an embodiment, the plurality of microneedles may be bent perpendicularly to the microneedle plate while the microneedle plate rests on the first head part.

In an embodiment, the plurality of microneedles may be bent simultaneously.

According to an embodiment of the present invention, provided is a microneedle part used in the cosmetic injector, on which microneedles for inducing absorption of cosmetics are mounted.

Advantageous Effects

The present invention has the effect of providing a cosmetic injector in which a microneedle can be easily mounted on a head part.

Also, the present invention has the effect of preventing a microneedle mounted on a head part from being broken.

Also, the present invention has the effect of preventing a microneedle from being contaminated by an operator when a cosmetic injector is manufactured.

MODE FOR CARRYING OUT THE INVENTION

Hereinafter, a cosmetic injector, on which microneedles for inducing absorption of cosmetics are mounted, will be described with reference to drawings.

As used herein, the term of "microneedle" may refer to an entire needle made of metal, and a portion thereof inserted into the skin may have a length of 1 mm or less.

Figure 1:
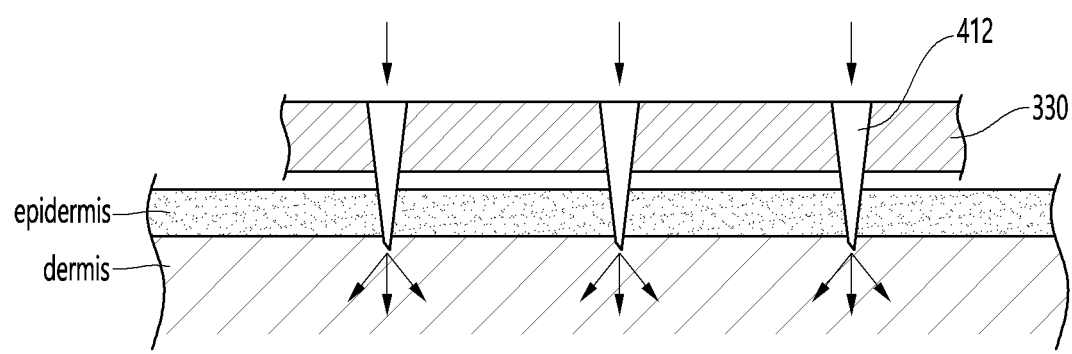
FIG. 1 shows a state in which cosmetics penetrate into the skin via a cosmetic injector.

FIG. 1 shows a state in which a plurality of microneedles 412 are inserted in to the dermis after passing through the epidermis, and cosmetics including nutrients may reach the dermis via the surfaces of the plurality of microneedles 412.

That is, when the microneedles 412 pierce the epidermis of the skin, the cosmetics may penetrate into a portion under the epidermis of the skin via the micropores which are formed in the epidermis of the skin by the microneedles 412.

Figure 2A:
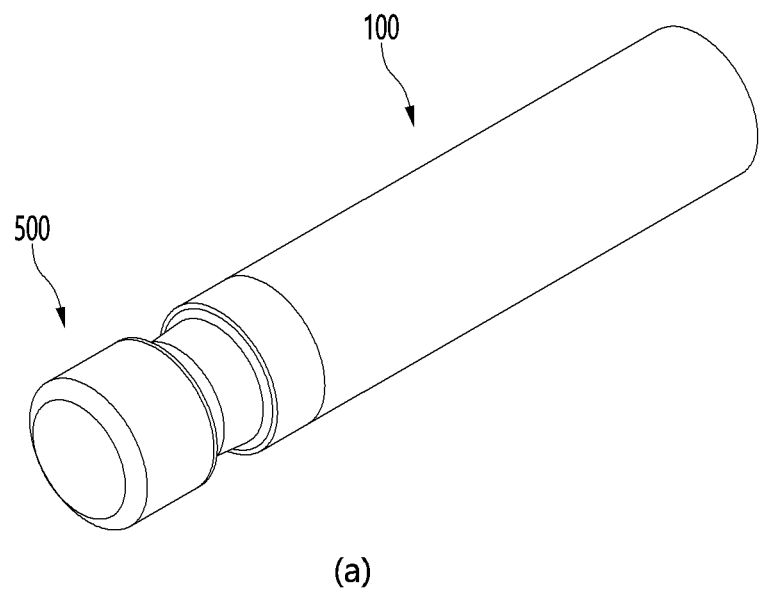
FIG. 2(a) is a perspective view of a cosmetic injector, on which microneedles for inducing absorption of cosmetics are mounted, according to the present invention.
Figure 2B:
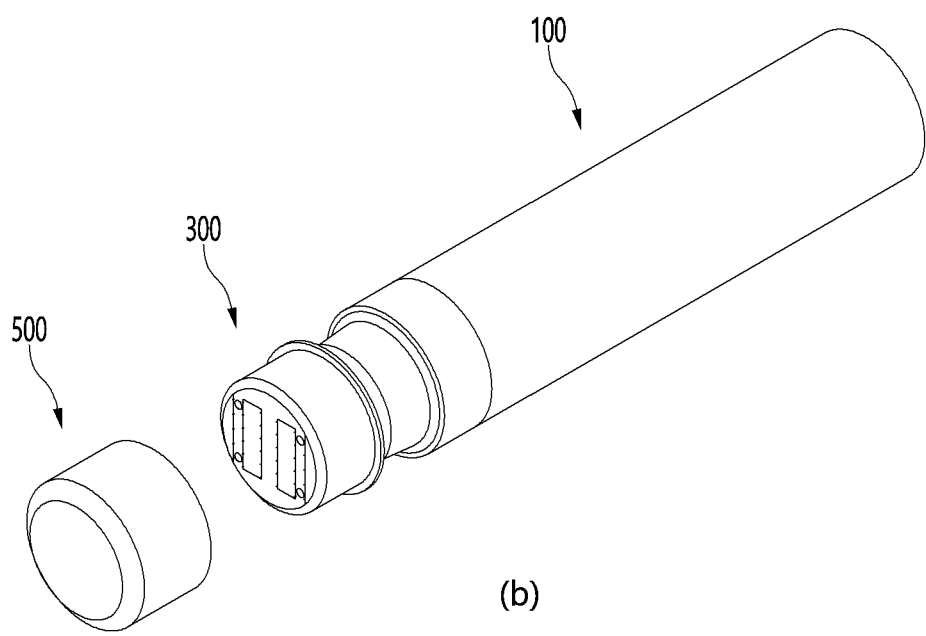
FIG. 2(b) is a perspective view of a cosmetic injector, on which microneedles for inducing absorption of cosmetics are mounted, according to the present invention and illustrates a state in which a cap part is open.

Referring to FIGS. 2(a) and 2(b) showing the perspective views of a cosmetic injector for absorbing cosmetics, the cosmetic injector, on which microneedles for inducing absorption of cosmetics are mounted, according to an embodiment of the present invention may include: an accommodation part 100 that accommodates cosmetics including nutrients; a head part 300 that has a flow path, through which the cosmetics flow in, and is in close contact with the skin; a pumping part 200 that transfers the cosmetics, which are accommodated in the accommodation part 100, to the head part 300; and a cap part 500 that selectively covers the head part.

Figure 3:
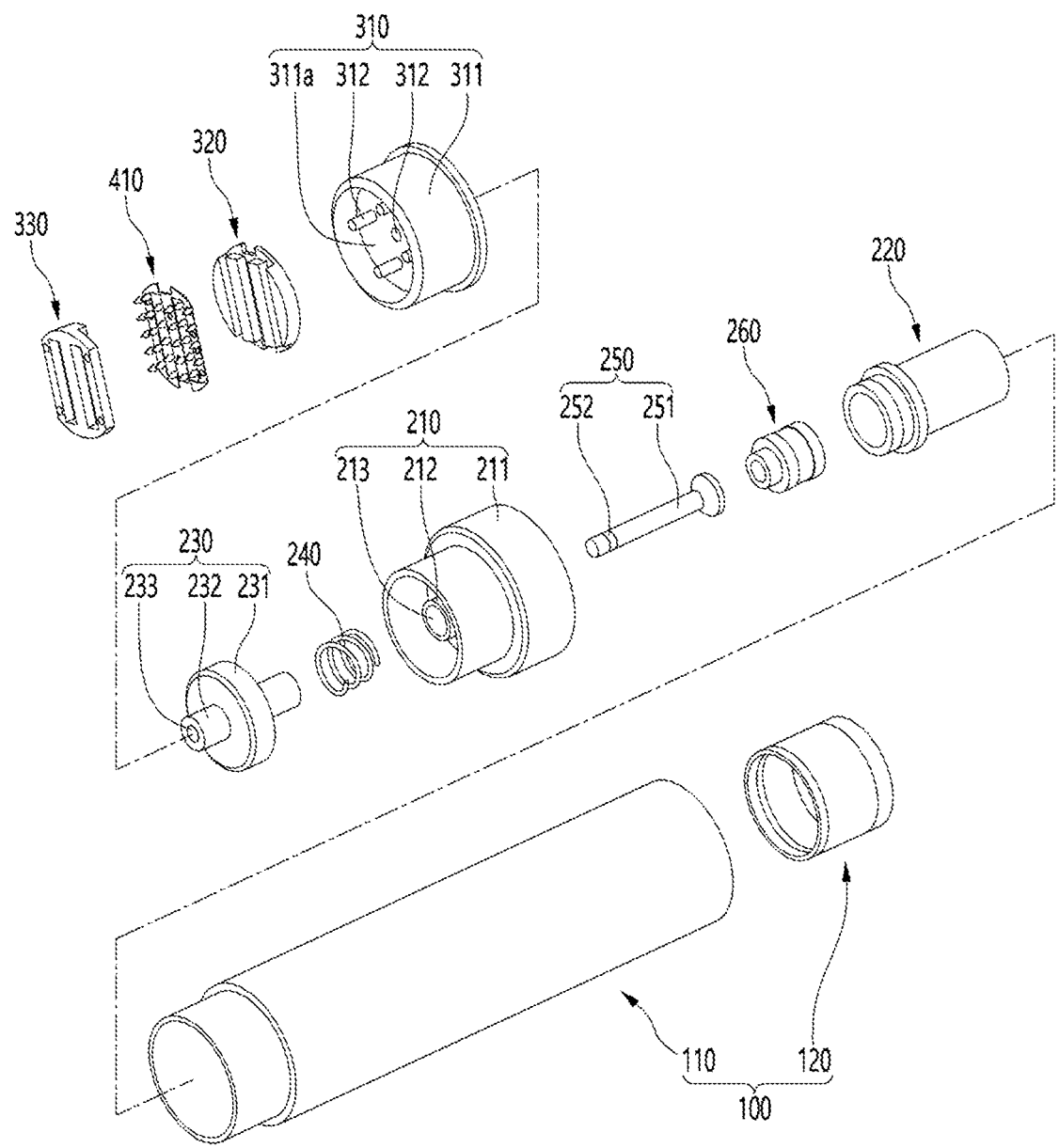
FIG. 3 is an exploded perspective view of the cosmetic injector, on which microneedles for inducing absorption of cosmetics are mounted, according to the present invention.

Hereinafter, detailed configurations of the cosmetic injector according to an embodiment of the present invention, on which microneedles for inducing absorption of cosmetics are mounted, will be described with reference to FIG. 3.

First, the accommodation part 100 may include: an accommodation part body 110 for accommodating the cosmetics; and a bottom part 120 which is internally fitted to the accommodation part body 110 and maintains the level inside the accommodation part body 110 so that the cosmetics are discharged.

Next, the pumping part 200 may include: a fixed case 210 fixed to the accommodation part body 110; a pumping case 220 which receives the cosmetics from the accommodation part body 110, temporarily stores the cosmetics, and then guides the cosmetics to the head part 300; a press part 230 that is lowered as the head part 300 is pressed; a spring 240 connected so that the press part 230 is elastically supported by the fixed case 210; a push rod 250 which is raised or lowered by the press part 230 and transfers the cosmetics inside the pumping case 220 to the head part 300; and a sealing cap 260 for forming a seal between the push rod 250 and the pumping case 220.

The fixed case 210 may include: a fixed case body 211 having a cylindrical shape and fixed to the accommodation part body 110; and a press part insertion 212 into which the press part is inserted and which has a coupling hole 213 that is a flow path through which the cosmetics move.

Also, the press part 230 may include: a press part body 231 supported by the spring 240; and an insertion part 232 which is provided in the press part body 231, has a discharge hole 233 serving as a path for moving the cosmetics, and is inserted into the head housing 310 and the coupling hole 213.

The push rod 250 may include: a push rod body 251 having a cylindrical shape and a bore that serves as a path through which the cosmetics move; and an annular groove 252 formed in the outer circumference of the push rod body 251.

The head part 300 may include: a first head part 320 for receiving the cosmetics from the pumping part 200; a second head part 330 which is coupled to the upper portion of the first head part 320 and fixes the microneedle part 410 to the first head part 320; and a head housing 310 for accommodating the first head part 320, the second head part 330, and the microneedle part 410.

The head housing 310 may include: a head housing body 311 which has a cylindrical outer circumference and forms a resting part 311a for accommodating the first head part 320, the second head part 330, and the microneedle part 410; a fixing protrusion 312 which protrudes upward from the middle wall of the head housing body 311 and fixes the positions of the first head part 320, the second head part 330, and the microneedle part 410; and a head housing flow path 313 which is formed inside the head housing body 311 and guides the cosmetics to the first head part 320.

Figure 4:
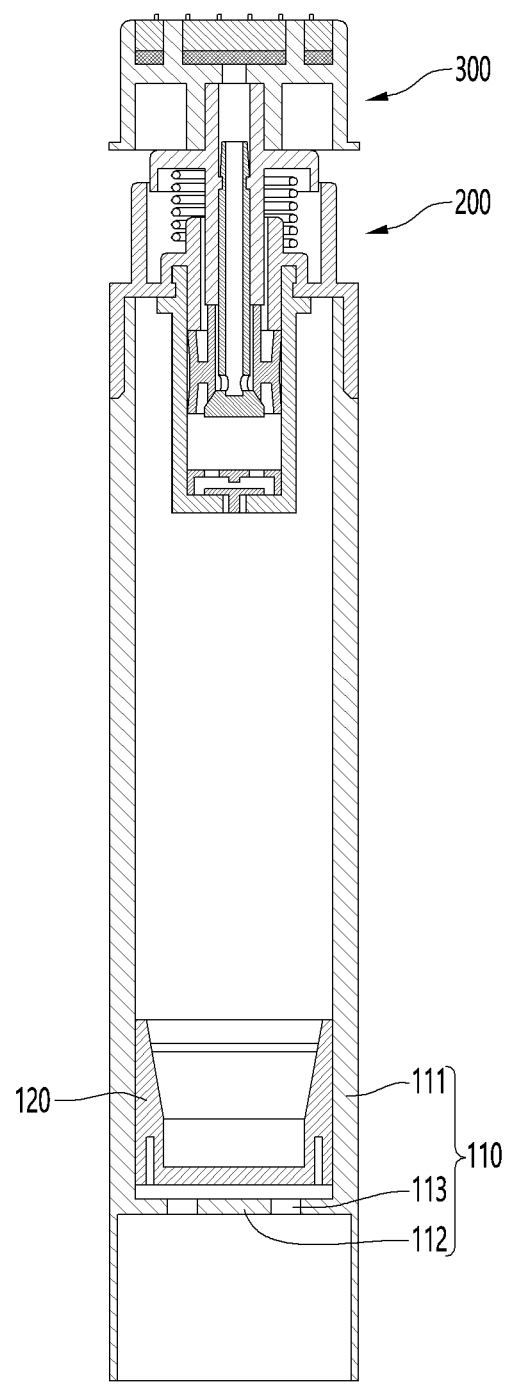
FIG. 4 is a cross-sectional view of the cosmetic injector, on which microneedles for inducing absorption of cosmetics are mounted, according to the present invention.

Hereinafter, detailed configurations of the accommodation part 100 will be described with reference to FIG. 4.

An accommodation part body 110 of the accommodation part 100 may include: a main body 111 having a cylindrical shape and accommodating the cosmetics; a partition wall 112 for preventing the bottom part 120 from separating from the lower portion of the accommodation part body 110; and a partition wall ventilation opening 113 which is formed in the partition wall 112 and allows the bottom part 120 to communicate with the atmosphere and the main body 111 so that the bottom part 120 is lifted.

The bottom part 120 has an approximately cup shape, and is inserted into the main body 111 and brought into contact with the inner circumferential surface of the main body 111.

Also, the cosmetics are accommodated between the pumping part 200 and the bottom part 120, and the bottom part 120 may be moved toward the pumping part 200 by atmospheric pressure when the cosmetics are discharged to the outside of the main body 111 by the pumping part 200.

Figure 5:
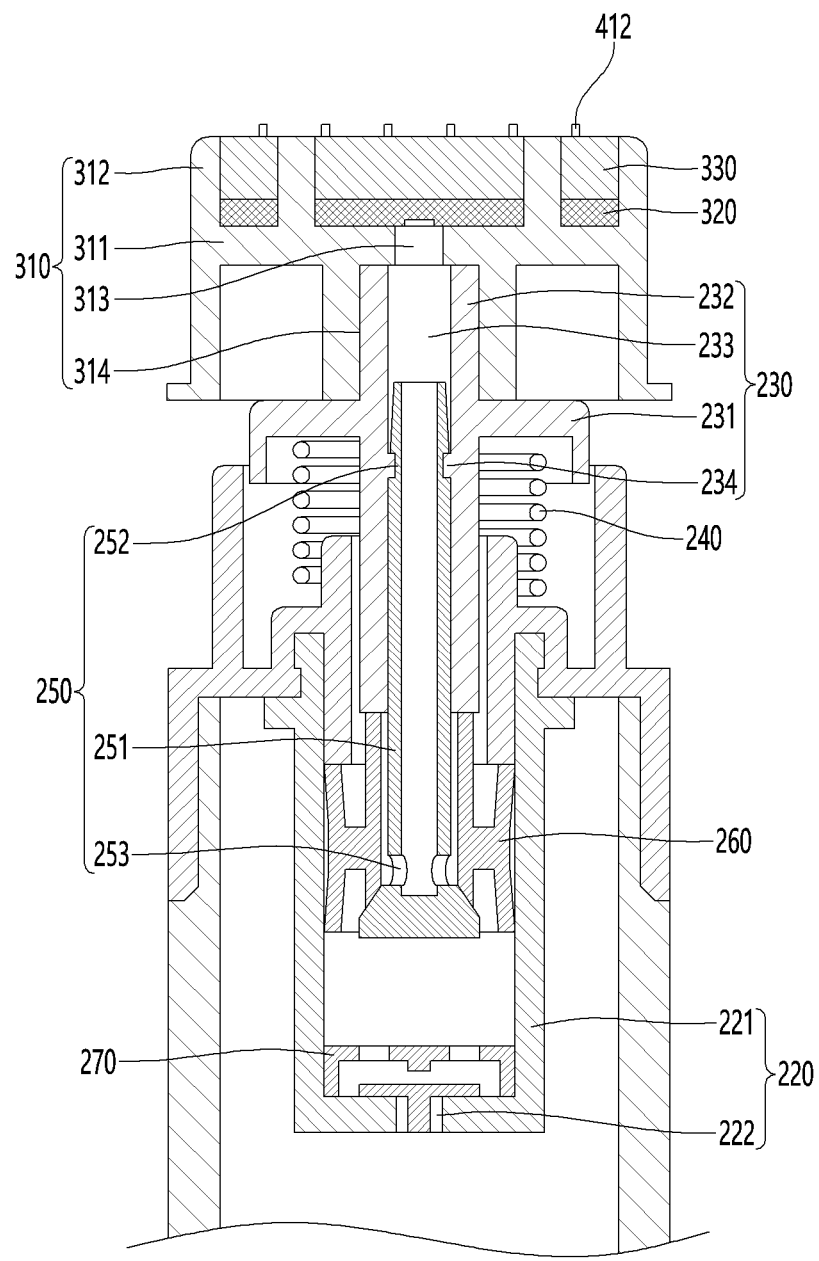
FIG. 5 is a cross-sectional view of a head part included in the cosmetic injector, on which microneedles for inducing absorption of cosmetics are mounted, according to the present invention.

Hereinafter, a structure for discharging the cosmetics from the accommodation part 100 to the head part 300 and a coupling relationship thereof will be described with reference to FIG. 5.

The pumping case 220 may include: a pumping case body 221 which is coupled to the fixed case 210 and in which the cosmetics temporarily stays; and an inflow hole 222 which is provided in the lower portion of the pumping case body 221 and through which the cosmetics in the main body 111 flow in.

Also, the cosmetic injector according to an embodiment of the present invention, on which microneedles for inducing absorption of cosmetics are mounted, may further include a check valve 270 which is coupled to the inner lower portion of the pumping case body 221 and selectively opens and closes the inflow hole 222.

The check valve 270 may open the inflow hole 222 due to negative pressure when the cosmetics accommodated in the main body 111 flow in the pumping case body 221, and then may block the inflow hole 222 to prevent the cosmetics, which has flowed in the pumping case body 221, from being discharged again to the main body 111.

The insertion part 232 of the press part 230 is positioned above the pumping case 220 and inserted into the coupling hole 213, and may move in the up-down direction along the coupling hole 213.

The discharge hole 233 formed inside the insertion part 232 of the press part 230 communicates with the pumping case 220 via the push rod 250.

Also, the spring 240 is located between the press part body 31 of the press part 230 and the fixed case body 211 and may elastically support the press part body 31 upward.

The push rod 250 is coupled to the press part 230, and a lower portion thereof may be located inside the pumping case body 221.

A press protrusion 234 of the press part 230 may be fastened to the annular groove 252 of the push rod 250.

Also, a pumping hole 253 is formed in a lower portion of the push rod body 251 located inside the pumping case body 221, and the pumping hole 253 may be opened and closed by the sealing cap 260.

That is, the sealing cap 260 is formed surrounding the lower outer circumferential surface of the push rod 250, and as described above, may open the pumping hole 253 when the push rod 250 descends and close the pumping hole 253 again when ascending.

Specifically, when the press part 230 and the push rod 250 are lowered, a space between the push rod 250 and the sealing cap 260 is open, and the cosmetics accommodated in the pumping case body 221 flow into the bore of the push rod body 251 via the pumping hole 253. When the press part 230 and the push rod 250 are raised, the pumping hole 253 may be closed by the sealing cap 260.

The head housing 310 may further include a resting groove 314 which is formed in the lower portion of the head housing body 311 and into which the insertion part 232 is inserted, and the cosmetics, which have flowed in from the bore of the push rod body 251, may be guided to the head housing flow path 313 via the resting groove 314.

Figure 6:
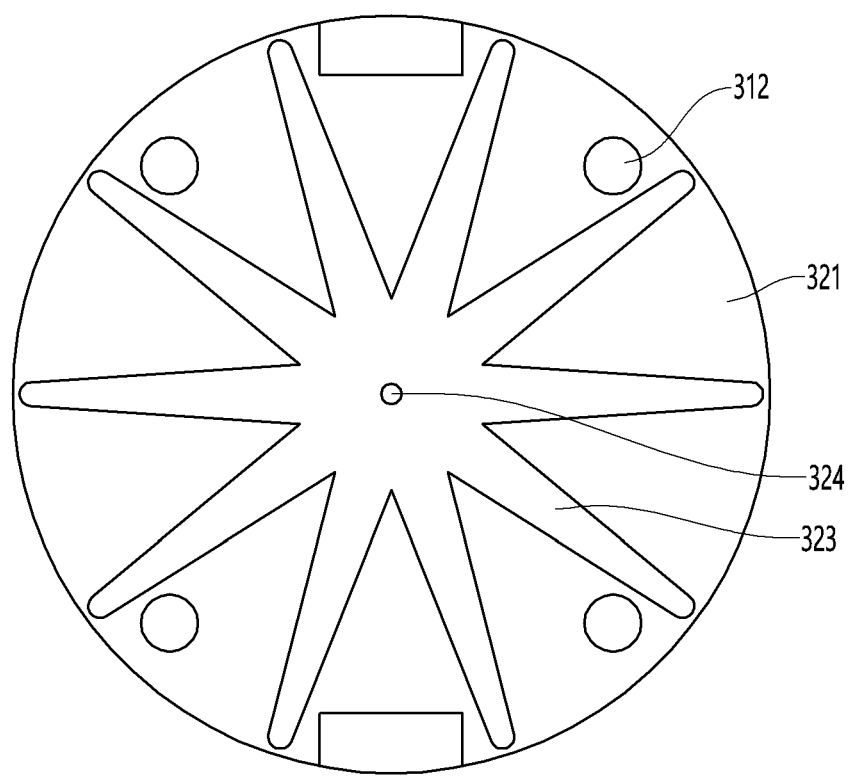
FIG. 6 is a plan view of the head part included in the cosmetic injector, on which microneedles for inducing absorption of cosmetics are mounted, according to the present invention.

FIG. 6 illustrates the lower surface of the first head part 320.

The first head part 320 may include: a guide hole 324 that vertically passes through the first head part body 321 and guides the cosmetics to the second head part; and a first head part flow path 324 that is recessed from the lower portion of the first head part body 321 and formed radially about the through-hole.

Accordingly, the cosmetics, which have flowed into the head housing 310 via the pumping part, may uniformly spread on the first head part flow path 324 having the radial shape and then flow to the guide hole 324.

That is, the first head part flow path 324 has the radial shape and temporarily stores the cosmetics and may serve to raise the pressure of the cosmetics that are discharged to the guide hole 324.

Figure 7:
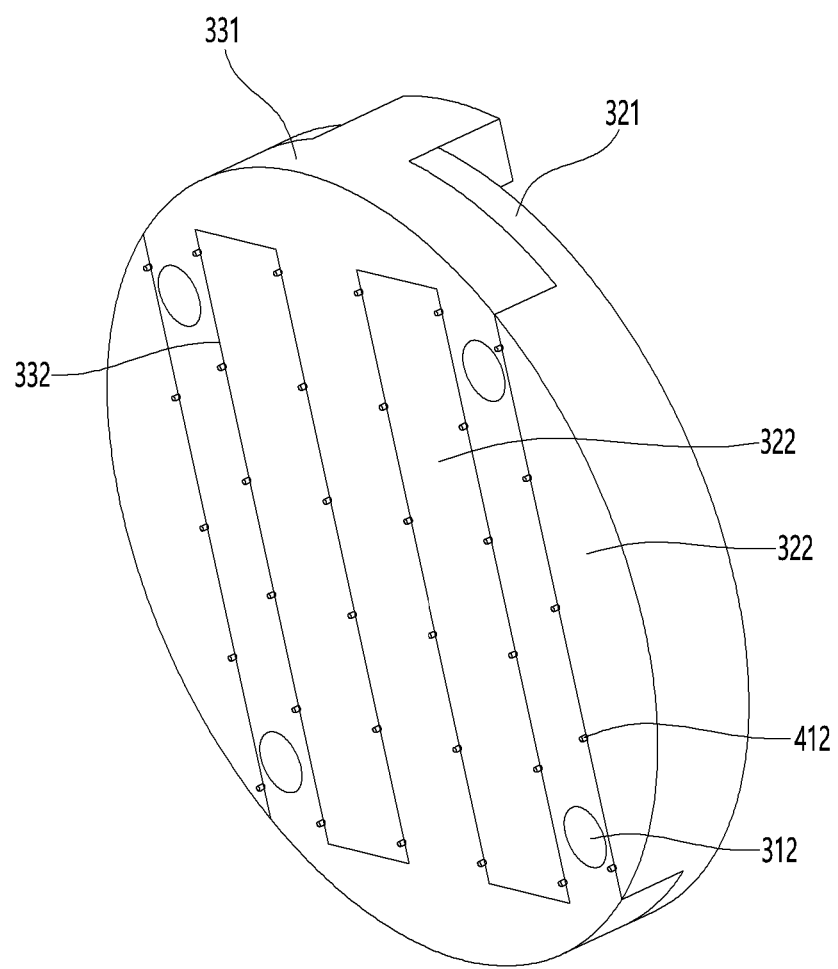
FIG. 7 is a perspective view of the head part included in the cosmetic injector, on which microneedles for inducing absorption of cosmetics are mounted, according to the present invention.

Hereinafter, detailed structures of the first head part 320 and the second head part 330 will be described with reference to FIG. 7.

The first head part 320 may include the first head part body 321 having a disc shape and a resting protrusion 322 protruding upward from the first head part body 321. The resting protrusion 322 may be provided in plurality.

Also, the second head part 330 may include a second head part body 331 coupled to the first head part body 321 and a resting protrusion coupling part 332 serving as a hole into which the resting protrusion 322 and the plurality of microneedles 412 are inserted. The resting protrusion coupling part 332 may be provided in plurality.

Figure 8:
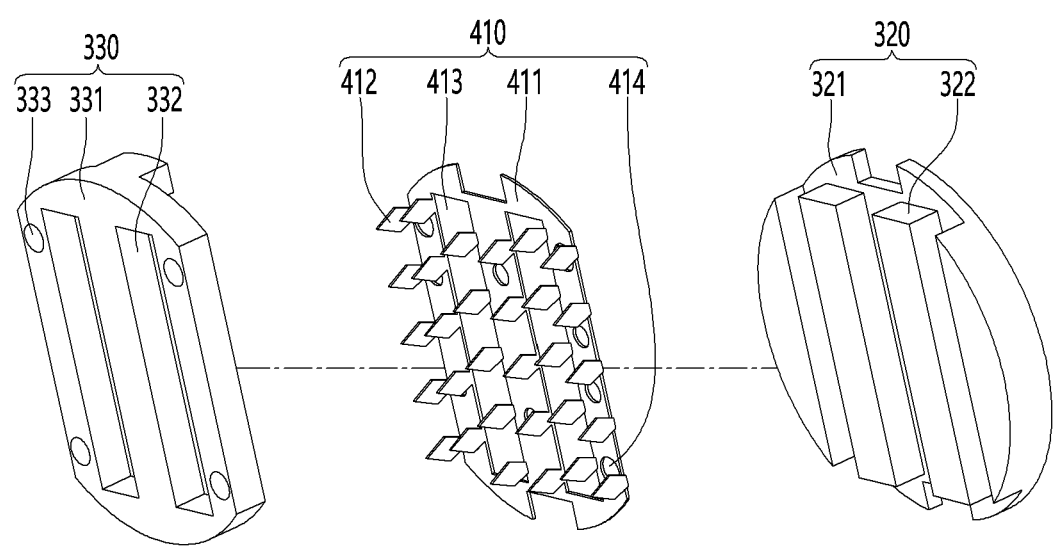
FIG. 8 is an exploded perspective view of the head part included in the cosmetic injector, on which microneedles for inducing absorption of cosmetics are mounted, according to the present invention.

The detailed structure of the microneedle part 410 and the coupling relationship between the first head part 320 and the second head part 330 will be described with reference to FIG. 8.

The microneedle part 410 may include: a microneedle plate 411 coupled between the first head part body 321 and the second head part body 331; and a plurality of microneedles 412 which extend from the microneedle plate 411, protrude toward the upper surface of the second head part 330, and guide the cosmetics, discharged from the head part, into the skin.

Also, a resting protrusion through-hole 413, into which the resting protrusion 322 is inserted, may be formed in the microneedle plate 411. The plurality of microneedles 412 extend laterally from the resting protrusion through-hole 413 and the edge of the microneedle plate 411 and then bent, and thus may be perpendicular to the microneedle plate 411.

The microneedle part 410 may be made of metal so that contact points between the microneedle plate 411 and the plurality of microneedles 412 can be pressed and bent by the resting protrusion, and the microneedle plate 411 and the plurality of microneedles 412 may be integrally formed.

Accordingly, the present application can enhance coupling and durability of the microneedle part 410 and thus easily prevent breakage of microneedles that occurs in a cosmetic injector in which microneedles according to the related art are mounted.

In addition, the present application eliminates the need to manually install each of a plurality of microneedles in the head part, thereby reducing working costs and preventing each of the microneedles from being contaminated due to the manual work of an operator during the manufacturing process.

Meanwhile, the first head part 320 may further include a first head part fixing protrusion insertion hole (not shown) through which the fixing protrusion 312 of the head housing 310 passes, the microneedle part 410 may further include a microneedle part fixing protrusion insertion hole 414 through which the fixing protrusion 312, which has passed through the first head part fixing protrusion insertion hole, passes, and the second head part 330 may further include a second head part fixing protrusion insertion hole 333 through which the fixing protrusion 312, which has passed through the microneedle part fixing protrusion insertion hole 413, passes.

Accordingly, the microneedle part 410 may rest at the right position between the first head part 320 and the second head part 330, and thus assemblability may be improved.

Here, the fixing protrusion 312, the first head part fixing protrusion insertion hole, the microneedle part fixing protrusion insertion hole 414, and the second head part fixing protrusion insertion hole 333 may be provided in plurality.

Figure 9:
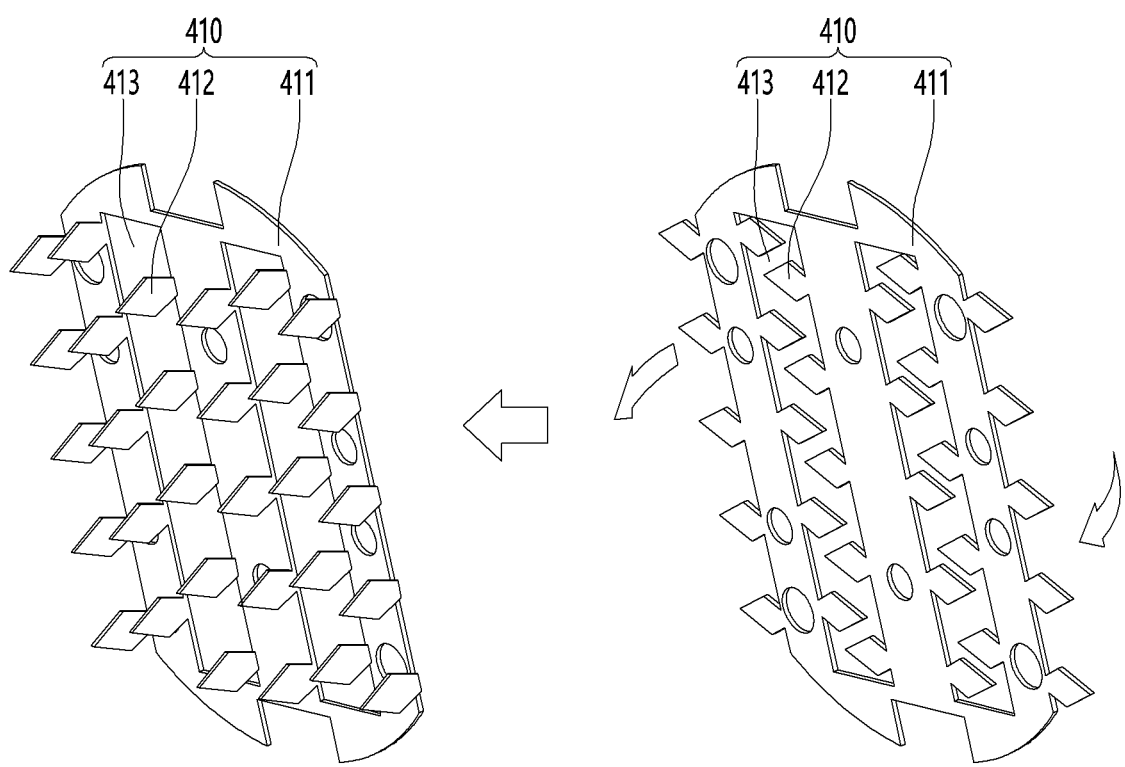
FIG. 9 illustrates a process of bending microneedles of a microneedle plate included in the cosmetic injector, on which microneedles for inducing absorption of cosmetics are mounted, according to the present invention.

FIG. 9 illustrates a process in which the microneedle part 410 is bent when a product is assembled.

First, the plurality of microneedles 412 extend toward the edge of the microneedle plate 411 and the resting protrusion through-hole 413 and formed horizontally with the microneedle plate 411.

Subsequently, the plurality of microneedles 412 are pressed upward by the resting protrusion 322 while resting on the first head part 320, and thus bent in a direction perpendicular to the microneedle plate 411.

That is, when the microneedle plate 411 is pressed downward against the first head part 320 by another mechanism, on which the microneedle plate 411 rests, or the second head part 330, the plurality of microneedles 412 may be simultaneously bent upward and then inserted into the resting protrusion coupling part 332, and thus may be positioned between the resting protrusion 322 and the second head part body 331.

Figure 10:
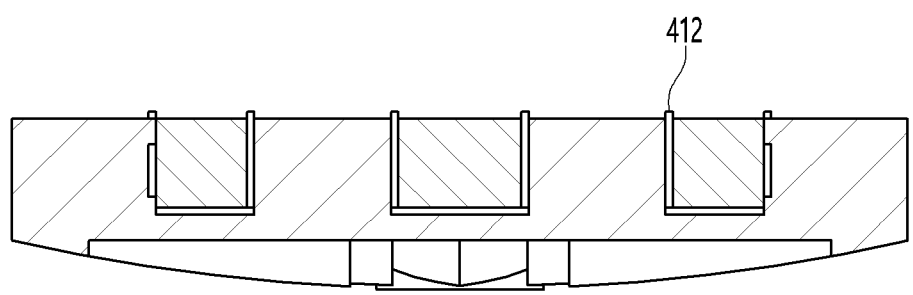
FIG. 10 illustrates the upper side of the head part of the cosmetic injector, on which microneedles for inducing absorption of cosmetics are mounted, according to the present invention.

Subsequently, the vertically bent microneedles 412 pass through gaps (see FIG. 10) formed between the resting protrusion 322 and the resting protrusion coupling part 332 and protrude above the second head part 330.

When the gaps for accommodating microneedles are formed, the microneedle are fixed, and bending of the microneedles is prevented. Moreover, the cosmetics may be smoothly discharged to the outside of the head part via the through-holes formed between the microneedles.

Also, the length of each of the plurality of microneedles 412 may be greater than the distance from the upper surface of the first head part body 321 to the upper surface of the second head part body 331. The length of the microneedle 412 protruding upward from the second head part may be preferably 0.001 to 2 mm.

When the length of a portion of the end of the microneedle 412, which protrudes upward from the second head part 330, is less than 0.001 mm, there is almost no skin penetration effect of cosmetics. When the length is greater than 2 mm, the capillaries may rupture, and bleeding may occur. Therefore, the protrusion length thereof is preferably limited to the above-mentioned range.

When the length of the bent microneedle is greater than the distance from the resting part to the upper surface of the head part, the microneedle may be allowed to protrude to the outside of the head part. Moreover, the microneedle is supported by the second head part, and thus durability thereof may be enhanced.

The microneedle part 410 may be preferably manufactured by cutting a plate, more preferably manufactured by cutting a metal plate, even more preferably manufactured by press or laser cutting a metal plate, or most preferably manufactured by press cutting a metal plate.

Next, the operation and use method of the cosmetic injector, on which microneedles for inducing absorption of cosmetics are mounted, according to an embodiment of the present invention will be described.

First, the cap part 500 is separated from the head part 300, and the second head part 330 is brought into contact with the skin. Then, when the accommodation part body 110 is pressed toward the second head part 330, the second head part 330 is brought into close contact with the skin. The microneedles 412 pierce the epidermis of the skin, and the tip ends are inserted below the epidermis.

During this process, the spring 240 is compressed as the press part 230 moves toward the pumping case 220, and a gap is made between the push rod 250 and the sealing cap 260. The cosmetics accommodated inside the pumping case 220 are allowed to flow into the push rod 250 via the pumping hole 253. Here, the inflow hole 222 is blocked by the check valve 270.

The cosmetics, which have flowed into the push rod 250 through this process, are transferred to the first head part flow path 323 via the discharge hole 233 and the head housing flow path 313.

Subsequently, the cosmetics flow to the central portion along the first head part flow path 323 and are then transferred to the second head part 330 via the guide hole 324. The cosmetics arriving at the second head part 330 may be discharged to the outside of the second head part via the gaps formed between the resting protrusion 322 and the resting protrusion coupling part 332.

Subsequently, when the pressure applied on the accommodation part body 110 is released, the press part 230 is returned to the original position by the elastic force of the spring 240. At the same time, the push rod 250 and the sealing cap 260 move upward.

Here, the pumping hole 253 formed in the lower portion of the push rod 250 is blocked by the sealing cap 260, and the inflow hole 222 is opened by the check valve 270 as the pressure inside the pumping case 220 becomes lower.

Accordingly, the cosmetics accommodated inside the accommodation part body 110 are allowed to flow into the pumping case body 221 via the inflow hole 222, and the bottom part 120 moves upward, thereby always maintaining a state in which the space between the pumping part 200 and the bottom part 120 is completely filled with the cosmetics.

Next, a method for manufacturing the cosmetic injector, on which microneedles for inducing absorption of cosmetics are mounted, according to an embodiment of the present invention will be described.

The manufacturing method for the cosmetic injector may include: a resting operation (S1) of resting the microneedle plate on the upper surface of the first head part in a state in which the microneedle plate 411 and the plurality of microneedles 412 are provided parallel to each other; and a head part coupling operation (S2) of coupling the second head part 330 to the upper portion of the first head part 320.

Here, the plurality of microneedles 412 may be bent perpendicularly to the microneedle plate 411 while the microneedle plate 411 rests on the first head part 320 and is then coupled thereto.

When the microneedles are bent perpendicularly while the microneedle plate rests on the resting part, it is possible to obtain the effect of reducing the manufacturing cost by omitting a separate press process for bending the microneedles.

In the present invention, each of the above-described components may additionally have another effect, even if the effect is not described herein. Also, it is possible to derive a new effect that cannot be found in the related art according to the organic coupling relationship between the above-described components.

In addition, embodiments illustrated in the drawings may be modified and implemented in other forms. These modifications should be regarded as falling within the scope of the present invention when the modifications are carried out so as to include components in the claims or within the scope of equivalents thereof.

The invention claimed is:

1. A cosmetic injector, on which a plurality of microneedles for inducing absorption of cosmetics are mounted, the cosmetic injector comprising:
   an accommodation part configured to accommodate cosmetics;
   a head part having a flow path through which the cosmetics flow in;
   a microneedle part which is fixed to the head part, and which is insertable into the skin and allows the cosmetics to penetrate the skin; and
   a pumping part configured to transfer, to the head part, the cosmetics accommodated in the accommodation part,
   wherein the head part comprises:
   a first head part configured to receive the cosmetics from the pumping part; and
   a second head part coupled to an upper portion of the first head part,
   wherein the microneedle part comprises:
   a microneedle plate provided between the first head part and the second head part; and
   the plurality of microneedles which extend from the microneedle plate and protrude toward an upper surface of the second head part, and which guide, into the skin, the cosmetics discharged from the head part,
   wherein the plurality of microneedles is formed integrally and horizontally with the microneedle plate,
   wherein the first head part comprises:
   a first head part body having an upper surface on which the microneedle plate rests; and
   a resting protrusion having an upper surface portion horizontal to the microneedle plate and the upper surface of the first head part body, and a sidewall portion vertical to the upper surface portion, wherein the upper surface portion contacts the plurality of microneedles,
   wherein the microneedle plate has a resting protrusion through-hole through which the resting protrusion passes, and
   wherein the microneedle plate is made of metal so that, when the resting protrusion passes through the resting protrusion through-hole, the plurality of microneedles is pressed by the upper surface portion of the resting protrusion and bent in a vertical direction along the sidewall portion of the resting protrusion.

2. The cosmetic injector of claim 1, wherein the resting protrusion is provided in plurality.

3. The cosmetic injector of claim 1, wherein the plurality of microneedles extend upward from a vicinity of the resting protrusion through-hole of the microneedle plate or from edges of the microneedle plate.

4. The cosmetic injector of claim 1, wherein the second head part comprises a second head part body having a lower surface that contacts the microneedle plate, and
   the second head part body has a resting protrusion coupling part that is a hole into which the resting protrusion and the plurality of microneedles are inserted.

5. The cosmetic injector of claim 4, wherein gaps configured to accommodate the plurality of microneedles are formed between the resting protrusion coupling part and the resting protrusion or between the outer boundary of the second head part body and the resting protrusion.

6. The cosmetic injector of claim 5, wherein the length of each of the plurality of microneedles is greater than the distance from the upper surface of the first head part body to the upper surface of the second head part.

7. The cosmetic injector of claim 1, further comprising a head housing that accommodates the first head part, the second head part, and the microneedle part, and receives the cosmetics from the pumping part.

8. The cosmetic injector of claim 7, wherein the first head part body has:
- a guide hole that vertically passes through the first head part body; and
- a first head part flow path which is provided in a lower portion of the first head part body and formed radially about the guide hole,
- wherein the cosmetics, which have flowed into the head housing via the pumping part, are guided to the guide hole via the first head part flow path.

9. The cosmetic injector of claim 7, wherein the second head part comprises a second head part body having a lower surface that contacts the microneedle plate,
- wherein the head housing further comprises:
- a head housing body configured to accommodate the first head part, the second head part, and the microneedle part; and
- a fixing protrusion that protrudes from the head housing body,
- wherein the first head part further comprises a first head part fixing protrusion insertion hole through which the fixing protrusion passes,
- the microneedle part further comprises a microneedle part fixing protrusion insertion hole through which the fixing protrusion, which has passed through the first head part fixing protrusion insertion hole, passes, and
- the second head part further comprises a second head part fixing protrusion insertion hole through which the fixing protrusion, which has passed through the microneedle part fixing protrusion insertion hole, passes.

10. The cosmetic injector of claim 9, wherein the fixing protrusion is provided in plurality, and
- the number of each of first head part fixing protrusion insertion holes, microneedle part fixing protrusion insertion holes, and second head part fixing protrusion insertion holes corresponds to the number of fixing protrusions.

11. The cosmetic injector of claim 1, wherein when the head part is pressed toward the pumping part, the cosmetics, which have been supplied via the pumping part, are discharged via the outer circumferential surfaces of the plurality of microneedles.

* * * * *